US00PP24012P2

(12) United States Plant Patent
Hoof

(10) Patent No.: US PP24,012 P2
(45) Date of Patent: Nov. 5, 2013

(54) ***THUJA* PLANT NAMED 'GOLDEN ANNE'**

(50) Latin Name: *Thuja occidentalis*
Varietal Denomination: Golden Anne

(75) Inventor: Ralph Matheus Hoof, Zevenaar (NL)

(73) Assignee: Hoof Zevenaar, Zevenaar (NL)

( * ) Notice: Subject to any disclaimer, the term of this patent is extended or adjusted under 35 U.S.C. 154(b) by 19 days.

(21) Appl. No.: 13/506,864

(22) Filed: May 21, 2012

(51) Int. Cl.
*A01H 5/00* (2006.01)

(52) U.S. Cl.
USPC ..... Plt./213

(58) Field of Classification Search
USPC ..... Plt./213
See application file for complete search history.

*Primary Examiner* — Kent L Bell
(74) *Attorney, Agent, or Firm* — Penny J. Aguirre

(57) ABSTRACT

A new cultivar of *Thuja occidentalis* named 'Golden Anne' characterized by its dense yellow-green foliage, its compact growth habit, and its moderate growth rate.

2 Drawing Sheets

Botanical classification: *Thuja occidentalis*.
Varietal denomination: 'Golden Anne'.

BACKGROUND OF THE INVENTION

The present invention relates to a new and distinct cultivar of *Thuja occidentalis* and will be referred to hereafter by its cultivar name, 'Golden Anne'. 'Golden Anne' represents a new western cedar, an evergreen shrub grown for landscape use.

The new *Thuja* was discovered by the Inventor as a naturally-occurring whole plant mutation in a trial garden in Zevenaar, The Netherlands in 2003. The parents are unknown and all plants of *Thuja occidentalis* growing in the area were unnamed.

Asexual reproduction of the new cultivar was first accomplished by softwood cuttings in Zevenaar, Netherlands in 2003 by the Inventor. Further generations of propagation has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Golden Anne', as unique from all other selections and forms of *Thuja occidentalis* known to the Inventor.

1. 'Golden Anne' exhibits yellow-green foliage.
2. 'Golden Anne' exhibits dense foliage.
3. 'Golden Anne' exhibits a compact growth habit.
4. 'Golden Anne' exhibits a moderate growth rate.

'Golden Anne' can be compared to plants of *Thuja occidentalis* that are typical of the species that were growing in the area. These plants differ in being taller in height, in having a more open and less densely branched plant habit, in being much more vigorous growth habit, and in having foliage that is green in color. 'Golden Anne' can be most closely compared to the cultivars 'Yellow Ribbon' (not patented) and 'Thusid1' (U.S. Plant Pat. No. 22,003). 'Yellow Ribbon' differs from 'Golden Anne' in having a relatively loose plant habit, being less densely branched and having foliage that is more yellow in color. 'Thusid1' differs from 'Golden Anne' in having yellow foliage only on the new growing tips, in having a columnar plant habit, and in having finer textured foliage.

BRIEF DESCRIPTION OF THE DRAWING

The plant and plant parts depicted in the accompanied photographs illustrate the characteristics of 'Golden Anne'. The photographs were taken of a six year-old plant as grown outdoors in 15-liter container in Zevenaar, the Netherlands.

Figure 1:
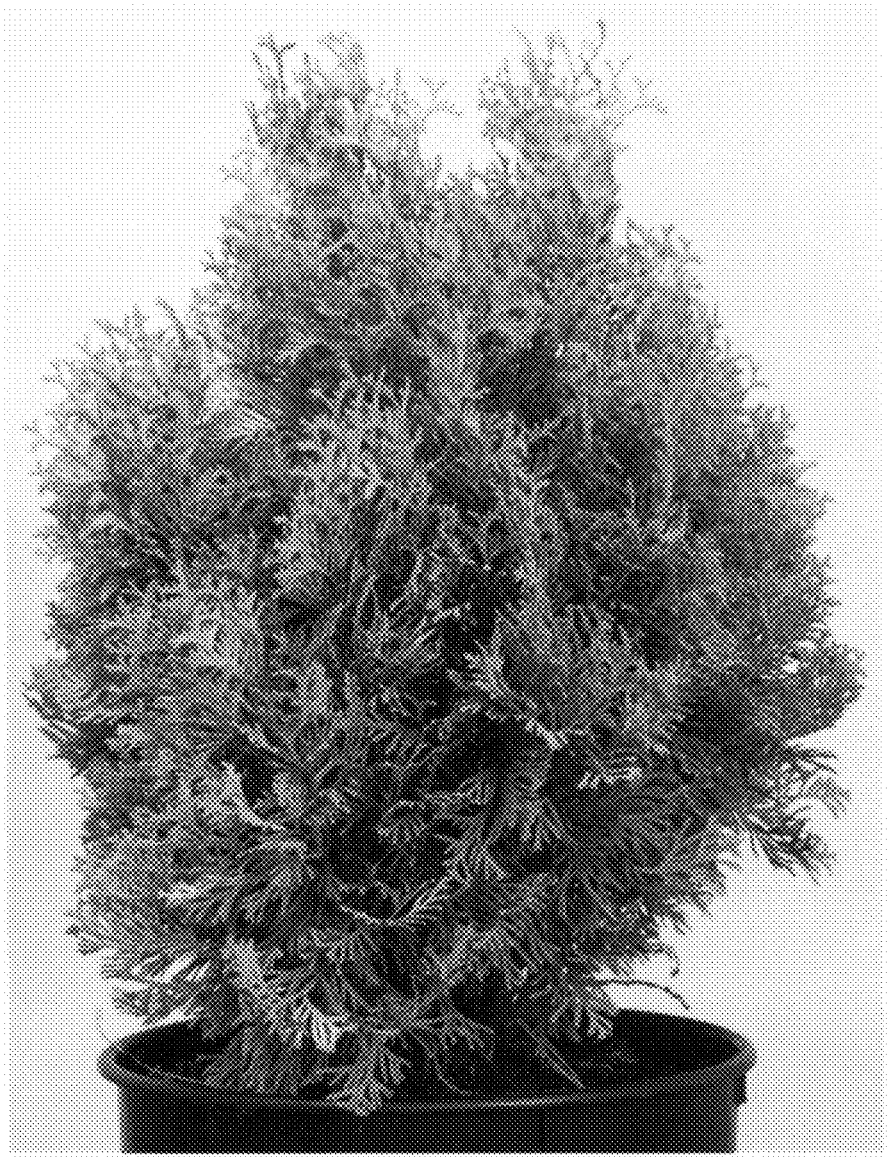
FIG. 1 provides an overall view of the compact habit of 'Golden Anne'.
Figure 2:
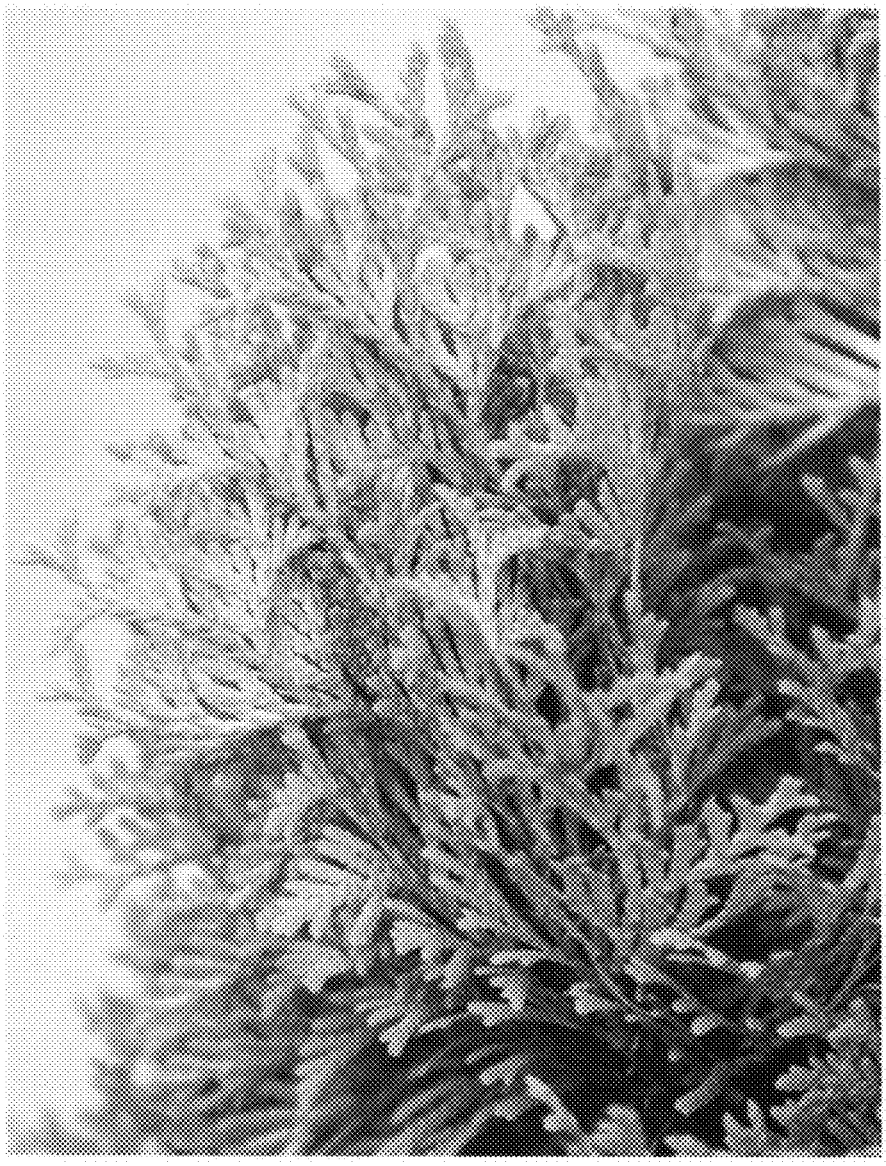
FIG. 2 provides a close-up view of the foliage of 'Golden Anne'.

The colors in the photographs are as close as possible with the digital photography and printing techniques utilized and the color codes in the detailed botanical description accurately describe the colors of the new *Thuja*.

DETAILED BOTANICAL DESCRIPTION

The following is a detailed description of the new cultivar as taken from six year-old plants grown outdoors in 15-liter containers in Zevenaar, The Netherlands with average day temperatures ranging from 10° to 20° C. and average night temperatures ranging from 1° to 12° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Coniferous, evergreen, shrub for landscape use.

*Growth habit.*—Broad upright, compact, oval-shaped with dense foliage.

*Height and spread.*—An average of 52.5 cm in height and 44 cm in width.

*Plant shape.*—Ovate to conical.

*Cold hardiness.*—U.S.D.A. Zone 6.

*Diseases and pests.*—Not more susceptible to pests and diseases than other *Thuja occidentalis* varieties.

*Root description.*—Slightly fibrous, non-fleshy, moderately dense, and moderately thick.

*Growth rate.*—Moderate.

*Propagation.*—Softwood cuttings.

Stem description:

*Stem shape.*—Rounded.

*Stem size.*—Average of 32.3 cm in length and 5 mm in diameter.

*Stem surface.*—Moderately glossy and smooth.

*Branching.*—Very freely branching, average of 31 branches.

*Stem arrangement.*—Alternate (closely on twigs).

*Stem aspect.*—Strong, covered with scale-like leaves.

*Internode length.*—Average of 1.5 cm.

*Stem color.*—One year-old stems; N144A, mature bark; 199C strongly tinged with 183A.

Foliage description:

*Leaf arrangement.*—Opposite.

*Leaf attachment.*—Sessile.

*Leaf shape.*—Linear, scale-like.

*Leaf division.*—Simple.

*Leaf base.*—Cuneate.

*Leaf apex.*—Caudate.

*Leaf venation.*—Not visible.

*Leaf margins.*—Entire.

*Leaf fragrance.*—Scale-like leaves produce a moderately strong pleasant smell when crushed.

*Leaf surface.*—Upper and lower surfaces; smooth, glossy.

*Leaf color.*—Immature upper and lower surfaces; between 150B and 154A, mature upper and lower surfaces; 8B, foliage that is shaded inside the plant; 143A to 143B.

*Leaf size.*—An average of 6 mm in length and 1.75 mm in width.

*Leaf quantity.*—Average of 9,000 scale-like leaves per lateral branch.

*Leaf glands.*—Found on the bases of the scales; average of 0.5 mm in diameter, orbicular in shape and 143D in color.

Cones: Neither male nor female cones have been observed.

It is claimed:

1. A new and distinct cultivar of *Thuja* plant named 'Golden Anne' as herein illustrated and described.

* * * * *